(12) United States Patent
Oh et al.

(10) Patent No.: US 6,255,098 B1
(45) Date of Patent: Jul. 3, 2001

(54) DS11 (KCTC 0231BP), NOVEL BACILLUS SP. STRAIN AND NOVEL PHYTASE PRODUCED BY IT

(75) Inventors: Tae Kwang Oh; Hyung Kwon Kim; Kyung Suk Bae; Young Seo Park, all of Daejeon; Young Ok Kim, Pusan; Yang Woong Choi; Dong Kyu Lee, both of Seoul; Jung Kee Lee, Daejeon, all of (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/142,612

(22) PCT Filed: Mar. 14, 1997

(86) PCT No.: PCT/KR97/00040

§ 371 Date: Dec. 16, 1998

§ 102(e) Date: Dec. 16, 1998

(87) PCT Pub. No.: WO97/33976

PCT Pub. Date: Sep. 18, 1997

(30) Foreign Application Priority Data

Mar. 14, 1996 (KR) .................................................. 96-6817

(51) Int. Cl.⁷ .................................. C12N 1/20; C12P 1/06
(52) U.S. Cl. ........................................ 435/252.5; 435/196
(58) Field of Search .................................. 435/196, 252.5

(56) References Cited

FOREIGN PATENT DOCUMENTS

| 6-38745 | 5/1994 | (JP) . |
|---|---|---|
| WO 94/19 471 A1 | 1/1994 | (WO) . |

OTHER PUBLICATIONS

Shimizu, M., Biosci., Biotechnol., Biochem. (1992), 56(8), 1266–9.*

Powar et al., J. Bacteriol., vol. 151, p. 1102–1108, 1982.*

Ehrlich et al., Indentification and cloning of a second phytase gene (phyB) from *Aspergillus niger (ficuum)*, Biochem Biophy Res Commun 195:53–7 (1993).

Greiner, et al., Purification and Characterization of Two Phytases from *Escherichia coli*, Arch Biochem Biophys 303:107(1993).

Gibson, D.M., Some modification to the media for rapid automated detection of salmonellas by conductance measurement, J Appl Bacteriol 63(4):299–304 (1987).

Lei et al., Calcium level affects the efficacy of supplemental microbial phytase in corn–soybean meal diets of weanling pigs, J. Anim Sci 72(1):139–43 (1994).

Mroz et al., Apparent digestibility and retention of nutrients bound to phytate complexes as influenced by microbial phytase and feeding regimen in pigs, J Anim Sci 72(1):126–32 (1994).

Piddington et al., The Cloning and sequencing of the genes encoding phytase (phy) and pH 2.5–optimun acid phosphatase (aph) from *Aspergillus niger* var. *awamori*, Gene 133(1):55–62 (1993).

Sneath, P., Endospore–forming Gram–Positive Rods and Cocci, Bergey's Manual of Systematic Bacteriology 2:1104–1139 (1984).

Ullah., A.H., The complete primary structure elucidation of *Asperigillus ficuum (niger)*, pH 6.0, optimum acid phosphatase by Edman degradation, Biochem Biophy Res Commun 203(1):182–9 (1994).

Ullah, A.H., Production, Rapid Purification and Catalytic Characterization of Extracellular Phytase from *Aspergillus ficuum*, Prep Biochem 18:443–58 (1988).

Ullah, A.H., *Aspergillus ficuum* Phytase: Partial Primary Structure, Substrate Selectivity, and Kinetic Characterization, Prep Biochem 18:459–72 (1988).

Ullah, A.H., Immobilization of *Aspergillus ficuum* Phytase: Product Characterization of the Bioreactor, Prep Biochem 18:483–89 (1988).

Ullah, A.H., *Aspergillus ficuum* Extracellular PH 6.0 Optimum Acid Phosphatase: Purification, N–Terminal Amino Acid Sequence, and Biochemical Haracterization, Prep Biochem 18:37–65 (1988).

Young et al., Addition of microbial phytase to diets of young pigs, J Anim Sci 71(8):2147–50 (1993).

\* cited by examiner

*Primary Examiner*—Irene Marx
(74) *Attorney, Agent, or Firm*—Finnegan, Henderson, Farabow, Garrett & Dunner, LLP

(57) ABSTRACT

The strain Bacillus sp. DS11 (KCTC 0231BP) is disclosed and a phytase produced by DS11 having the following characteristics: optimum temperature: 65° C.; optimum pH: 7.0; molecular weight: 43,000 dalton; isoelectric point: 5.6; and a specified N-terminal amino acid sequence. The bacterial strain DS11 or the phytase it produces can be used as an animal feed additive.

3 Claims, 3 Drawing Sheets

SEQUENCE LISTING

```
<160> NUMBER OF SEQ ID NOS: 3

<210> SEQ ID NO: 1
<211> LENGTH: 15
<212> TYPE: PRT
<213> ORGANISM: Bacillus sp. DS 11
<220> FEATURE:
<223> OTHER INFORMATION: Xaa = any amino acid

<400> SEQUENCE: 1

Ser Asp Pro Tyr His Phe Thr Val Asn Ala Ala Xaa Glu Thr Glu
 1               5                  10                  15

<210> SEQ ID NO: 2
<211> LENGTH: 11
<212> TYPE: PRT
<213> ORGANISM: Escherichia coli

<400> SEQUENCE: 2

Ser Glu Pro Glu Leu Lys Leu Glu Ala Val Val
 1               5                  10

<210> SEQ ID NO: 3
<211> LENGTH: 12
<212> TYPE: PRT
<213> ORGANISM: Aspegillus ficuum
<220> FEATURE:
<223> OTHER INFORMATION: Xaa = any amino acid

<400> SEQUENCE: 3

Pro Ala Ser Arg Xaa Gln Ser Ser Cys Asp Thr Val
 1               5                  10
```

DS11 (KCTC 0231BP), NOVEL BACILLUS SP. STRAIN AND NOVEL PHYTASE PRODUCED BY IT

BACKGROUND OF THE INVENTION

1. Field of the Invention

This invention relates to a novel phytase produced from novel strain Bacillus sp. DS11 (KCTC 0231BP) and more precisely, to a novel strain Bacillus sp. DS11 and phytase enzyme enhancing the phosphate bioavailability present in grains supplied to monogastric animals.

2. Description of the Prior Art

Phytase is an enzyme to degrade phytic acid into phosphate and phosphate inositol. 50 to 70% of phosphate in grain used as livestock feeds exists in form of phytic acid but phytase is not present in monogastric animals such as hens and hogs, resulting in low phosphate availability.

Therefore undigested phytic acid(phytictaine) released to a water source became one of the serious environment contamination sources causing to eutrophication in small lakes or tides. With above consideration, because monogastric animals can't utilize phytic acid in their intestine phytic acid chelates to water due to chelation with a trace amount of minerals, amino acids and vitamins which are very important to the metabolism of livestock. These formed water-insoluble, undigestable chelate complexes released to feces change the environmental ecosystem to induce a serious environmental pollution.

In view of these situations, the application of phytase into the livestock feeds will reduce the supply of inorganic phosphate due to increase of phosphate bioavailibility in livestock, leading to economic benefits, and improving the availibility of phosphate, and other bioactive substances, leading to reduction of the environmental contamination.

By these reasons, the utilization of phytase in livestock is very important. A law regulating the amount of phosphate in animal waste was established in 1996 in Korea and in European countries it is already mandatory to add phytase in the feeds of animals.

The addition of phytase in the feeds may greatly improve the productivity of livestock by enhancing the availability of some bioactive substances (phosphate, calcium and zinc etc.) which, otherwise chelate with phytictaine and lose their activity.

As the result, the use of feeds containing phytase in livestock can enhance the availibility of feeds and reduce the environmental contamination caused by phosphate.

For the aforementioned benefits, intensive studies about phytase including the effects of phytase on animals Young et al., Addition of microbial phytase to diet of young pigs, *J Anim Sci* 71(8)2147–50 (1993); Lei et al., Calcium level affects the efficacy of supplemental microbial phytase in corn-soybean meal diets of weaning pigs, *J Anim Sci* 72(1) 139–43 (1994); and Mroz et al., Apparent digestibility and retention of nutrients bound to phytate complexes as influenced by microbial phytase and feeding regimen in pigs, *J Anim Sci* 27(1):126–32 (1994); Z. Mroz et al., 1994) have been performed mainly in Europe Ullah., A. H., The complete primary structure elucidation of *asperigillus ficuum* (niger), pH 2.5-optimum acid phosphatase by Edman degradation, *Biochem Biophy Res Commun* 203(1):182–89 (1994); Ehrlich, et al., Identification and cloning of a second phytase gene (phyB) from *Aspergillus niger* (ficuum); and Piddington et aL, The Cloning and sequencing of the genes encoding phytase (phy) and pH 2.5-optimum acid phosphatase (aph) from *Asperigillus niger* var. awamori, *Gene* 133(1):55–62 (1993).However, since phytase can cleave only a limited number of phosphates and it mostly produced by molds which have long growing period, it is uneconomical in terms of mass production. In addition, it is difficult to use the phytic acid as an additive for monogastric animals since it is unsuitable to their physiological mechanism.

SUMMARY OF THE INVENTION

Therefore, the inventor et al. have identified a novel phytase-producing microorganism among hundred kinds of molds, Actinomycetes, bacteria, etc., obtained from soils and barns throughout the country, in an effort to produce phytase having excellent enzymatic potency and shorten the production period compared with the conventional phytase. Because of the high enzymatic potency of this novel microorganism and its physiological suitability to use for monogastric animals and short period of kproduction compared to those of conventional enzymes the inventor et al. have judged that this enzyme has novelty and they have completed this invention.

The object of this invention is to provide novel strain Bacillus sp. DS11 (KCTC 0231BP) and phytase enzyme, which is suitable to use for monogastric animals with excellent properties and more shortened production period.

DETAILED DESCRIPTION OF THIS INVENTION

This invention relates to a novel phytase produced from novel strain Bacillus sp. DS11 (KCTC 0231BP) and particularly, to a novel strain Bacillus sp. DS11 and phytase enzyme enhancing the phosphate bioavailability present in grains supplied to monogastric animals. The novel strain Bacillus sp. DS11 (KCTC 0231BP) was deposited with the Korea Research Institute of Bioscience and Biotechnology Korean Collection for type cultures, Korean Patent Strain Deposit Associates, located in #52, Oun-dong, Yusong-ku Taejeon 305,333, Republic of Korea, on Feb. 1, 1996, under Deposit Accession Number KCTC0231BP.

This invention is described in detail as set forth hereunder:

This invention relates to novel strain Bacillus sp. DS11 (KCTC 0231BP).

Further, this invention includes its novel enzyme phytase whose N-terminal amino acid sequence is SEQ. ID NO: 1 under the following conditions:

Optimal temperature: 65° C.
Optimal pH: 7.0
Molecular weight: 43,000 dalton
Isoelectric point: 5.6

In addition, this invention includes a method to use said microorganism as feed additives.

This invention is described in more detail as set forth hereunder:

This invention relates to a novel strain Bacillus sp. DS11 (KCTC 0231BP) and novel phytase produced from said strain. The procedure for isolating and identifying said novel microorganism is as follows:

[Isolation of Novel Microorganisms]

From several thousands of strains obtained from soils and in barns throughout the country, a strain was isolated which has excellent resolution in phytase screen plate containing 15 g of D-glucose, 5 g of calcium phytate, 5 g of $NH_4NO_3$, 0.5 g of $MgSO_4·7H_2O$, 0.5 g of KCl, 0.01 g of $FeSO_4·7H_2O$, 0.01 g $MnSO_4·4H_2O$ and agar 15 g at pH 7.0/l.

[Identification of Novel Microorganism]

The morphological property of the strain isolated from the above procedure is as follows:

1) Morphological Property

Figure 1:
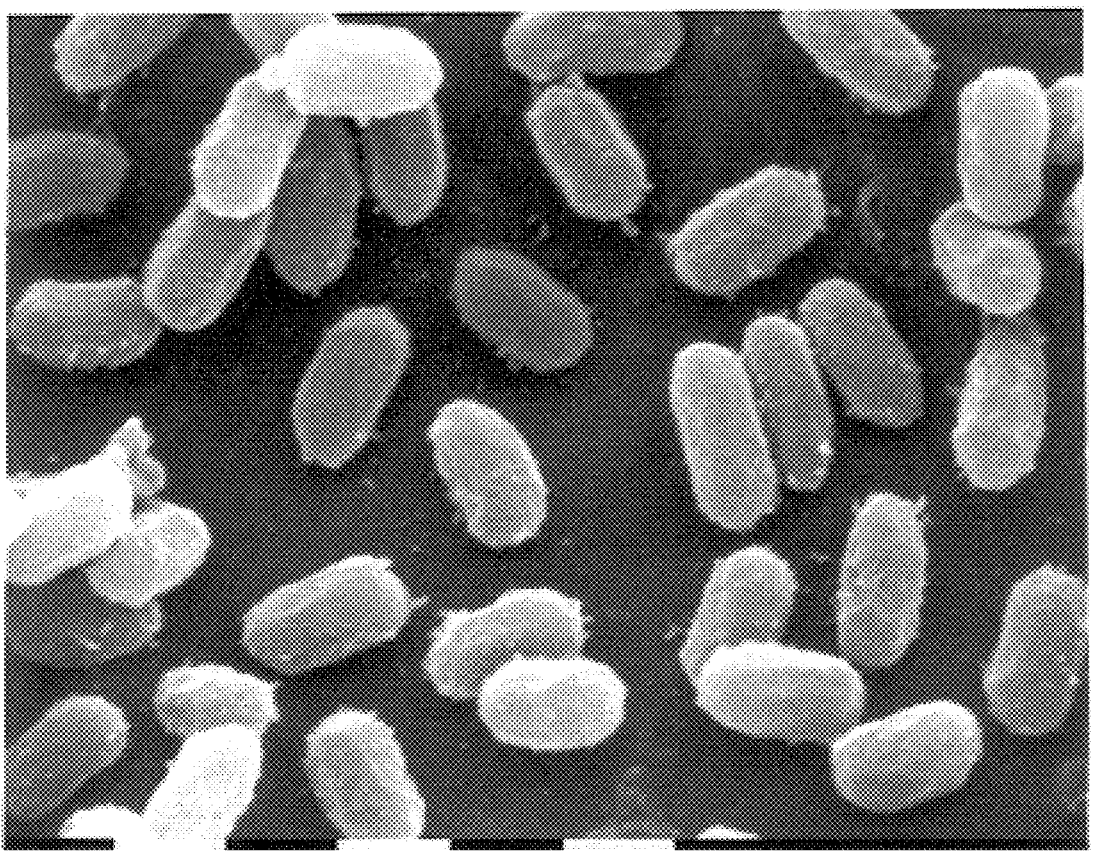
FIG. 1 is electron microscope photograph (×10,000) of Bacillus sp. DS11 (KCTC 0231BP) strain, a novel strain according to this invention.

In the grams staining test of the strain cultivated in an optimal growth medium, the strain was proven to be gram-positive. FIG. 1, the picture of electron microscope shows that strain is a rod type of 0.8~1.8 μm in cell size.

In the growth test of the thermally inactivated cells at 80° C., said strain has formed thermostable spores. Further, its catalase test in which it shows the positive response demonstrates that it coincides with the morphological property of Bacillus sp.

The physiological property of said strain is as follows:

2) Physiological Property

The test results of physiological property of the strain are represented in the following table 1. As shown in the table 1, it is assumed that strain is a facultative microorganism which may be grow in both aerobic and anaerobic states. With the difference of grown strains found at 50° C. and pH 5.7 compared with *Bacillus pantothenticus*, the strain of this invention is a mutant derived from *Bacillus pantothenticus*.

TABLE 1

| Property | | *Bacillus pantotheniticus* | Strain of this invention |
|---|---|---|---|
| Catalase | | + | + |
| Anaerobic culture | | + | + |
| V-p. test | | − | + |
| Acid-forming | glucose | + | + |
| | L-arabinose | − | + |
| | D-xylose | − | − |
| | D-mannitol | − | + |
| Hydrolysis | Casein | d | + |
| | Gelatin | + | + |
| | Starch | + | + |
| Synthesis | Indole | − | − |
| | Dihydroacetone | − | − |
| Growth pH | 6.8 | + | + |
| | 5.7 | − | + |
| Concentration of | 2% | + | + |
| growth salt | 5% | + | + |
| (at NaCl) | 7% | + | + |
| | 10% | + | + |
| Growth temperature | 5° C. | − | − |
| | 10° C. | − | − |
| | 30° C. | + | + |
| | 40° C. | + | + |
| | 50° C. | − | + |

Note) +: positive. −: negative. d: different from species.

The chemical property of the strain obtained as above is as follows:

3) The Chemical Property of Strain

After harvesting the strain, the test results of their various properties (e.g., G+C content, fatty acid composition, Murein Type and main melaquinone) are represented in the following table 2.

As shown in the above table 2, it is noted that the strain of this invention is similar to *Bacillus pantotheniticus* in terms of G+C content, murein type and main melaquinone including fatty acid of strain but it seems to difficult to make a judgement that both strains are the same species. Thus, it seems that the strain of this invention is a mutant derived from *Bacillus pantothenticus*.

TABLE 2

| Property | | *Bacillus pantotheniticus* | Strain of this invention |
|---|---|---|---|
| G + C content | | 36.9 | 45.6 |
| Murein type | | Mezo-DAP | Mezo-DAP |
| Main melaquinone | | MK-7 | MK-7 |
| Fatty acid of strain (%) | 14:0 ISO | 4.71 | 1.96 |
| | 14:0 | 1.50 | 1.21 |
| | 15:0 ISO | 19.34 | 18.72 |
| | 15:0 ANTEISO | 37.95 | 38.51 |
| | 16:0 ISO | 10.01 | 6.16 |
| | 16:0 | 9.77 | 9.77 |
| | 17:0 ISO | 4.37 | 9.02 |
| | 17:0 ANTEISO | 12.00 | 11.20 |
| | 18:0 | x | 2.03 |

By compiling above mentioned morphological, physiological and chemical properties, it is revealed that the strain of this invention belongs to Bacillus sp. from Sneath, P., Endospore-forming Gram-Positive Rods and Cocci, *Bergey's Manual of Systematic Bacteriology* 2:1104–1139 (1984). Therefore, the microorganism isolated was nominated as Bacillus sp. DS11 and deposited on Feb. 1, 1996, to Korea Research Institute of Bioscience and Biotechnology Korean Collection for type cultures, Korean Patent Strain Deposit Associations located in #52, Oun-dong, Yusong-ku, Taejeon 305–333, Republic of Korea, with an accession number KCTC 0231BP.

This invention is described in more detail by the following examples, but the claims are not limited to these examples.

EXAMPLE 1

Production of Novel Phytase

To produce phytase, a medium containing 6% wheat bran, $NH_2NO_3$ 0.04%, 0.02% $MgSO_4·7H_2O$, 1.0% casein hydrolysate, 0.05% $KH_2PO_4$, 0.04% $K_2HPO_4$ and 0.2% $CaCl_2$, was adjusted to pH 6.5 and sterilized at 121° C. for 15 minutes.

Then, with the same medium composition, 1% seed culture cultivated in a flask at 37° C. for 12 hours was inoculated into the medium in order to produce the enzyme.

The potency of produced enzyme was measured as follows: By using a substrate, comprising 2 mM phytic acid sodium salts and 2 mM $CaCl_2$ in 0.1 M Tris buffer solution (pH 7.0), the enzyme was reacted at 37° C. for 30 minutes to measure the amount of phosphoric acid generated. One unit of the enzymatic potency is equivalent to the enzymatic amount degrading 1 μ mol of inorganic phosphate per 1 minute. As a result of said measurement, the novel enzyme has the enzymatic potency of 0.3 unit per protein mg. The maximum amount of enzyme in fermentation yielding 0.6 unit/mg was obtained when 30 l of strains, a working volume, was charged to a 50 l fermenter and cultivated at 37° C. for 48 hours under the following conditions: air influx—0.8 vvm; stirring rate—150 rpm. Compared with the enzymatic production amount of 0.3 unit/mg when phytase enzyme derived from *Aspergillus ficuum* is cultivated for 96 hours [Gibson, D. M., Some modification to the media for rapid automated detection of salmonellas conductance measurement, *J Appl Bacteriol* 63(4):299–304 (1984)] it is well observed that the novel organism of this invention has a production amount twice higher.

Figure 2:
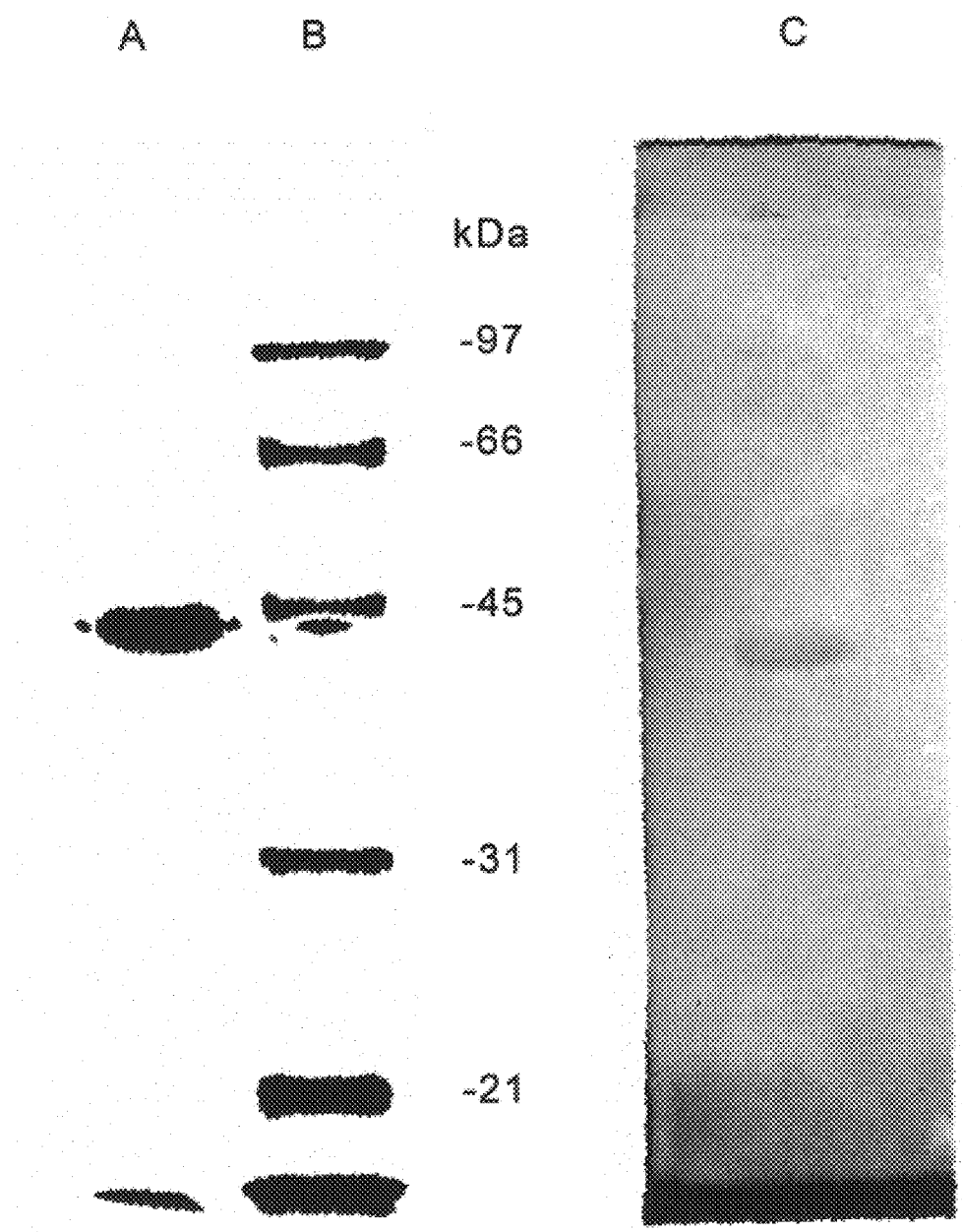
FIG. 2 is a SDS-PAGE electrophoresis analysis of novel phytase produced by Bacillus sp. DS11 (KCTC 0231BP), A: precipitation of acetone, B: resource S, C: superose 12 HR 10/30

EXPERIMENTAL EXAMPLE 1
Measurement of Molecular Weight for Novel Phytase 2 l of novel strain solution, cultivated according to the procedure as described in said Example, was centrifuged for 15 minutes. Then, the supernatant solution was saturated with 50% acetone to precipitate proteins and the crude enzyme solution passed through dialysis membrane was purified on a column containing phenyl sepharose CL-4B, Resource S and superose 12 HR 10/30 (all of which are manufactured by Pharmacia, Sweden) so as to isolate the phytase enzyme only. The analytical results by said column are represented in the attached drawing FIG. 2. Phytase enzyme was again on SDS-PAGE electrophoresis and the results show that the molecular weight of phytase produced by a novel strain is 43,000 dalton and isoelectric point is 5.6.

Further, the enzyme protein, so isolated, was used to determine the sequence of N-terminal amino acid using Protein/peptide Sequencer (Applied Biosystems, USA) and its results are represented in the sequence listing.

SEQ ID NO: 1 is the sequence of N-terminal amino acids of the phytase produced from a novel strain of this invention; SEQ ID NO: 2 is the sequence of the N-terminal amino acids of the phytase produced from *E. coli* [Greiner, et al., Purification and Characterization of Two Phytases from *Escherichia coli*, Arch Biochem Biophys 303:107(1993)]; SEQ ID NO: 3 is the sequence of the N-terminal amino acids of the phytase produced from *Aspegillus ficuum* [Ullah, A. H., *Aspergillus Ficuum* Phytase: Partial Primary Structure, Substrate Selectivity, and Kinetic Characterization, Prep Biochem 18:459–72 (1988)].

From the results of the sequence listing, it is revealed that the phytase enzyme produced by Bacillus sp. DS11 (KCTC 0231BP) of this invention is a novel enzyme.

EXPERIMENTAL EXAMPLE 2
Activity and Stability of Novel Phytase to Temperature and pH The optimal temperature was proved to be 65° C. by using the enzyme isolated by the same method as described in the experimental example 2. To measure the thermal stability, the enzyme was left at each temperature for 10 minutes so as to assess the residual activity. As shown in the attached drawing FIG. 3 (3-1), the results show that when $Ca^{2+}$ was not added, the activity began to decrease at 40° C. but in case of adding 5 mM calcium ion, the activity was stable up to 70° C. and 50% of the activity at 75° C. was sustained.

From the aforementioned results, a novel phytase of this invention may be expected to a higher activity in the body of livestock. Therefore, it seems to be preferable that the feeds should be pelleted or extruded at more than 75° C. so as to use them as processing ones.

Figures 1, 3:
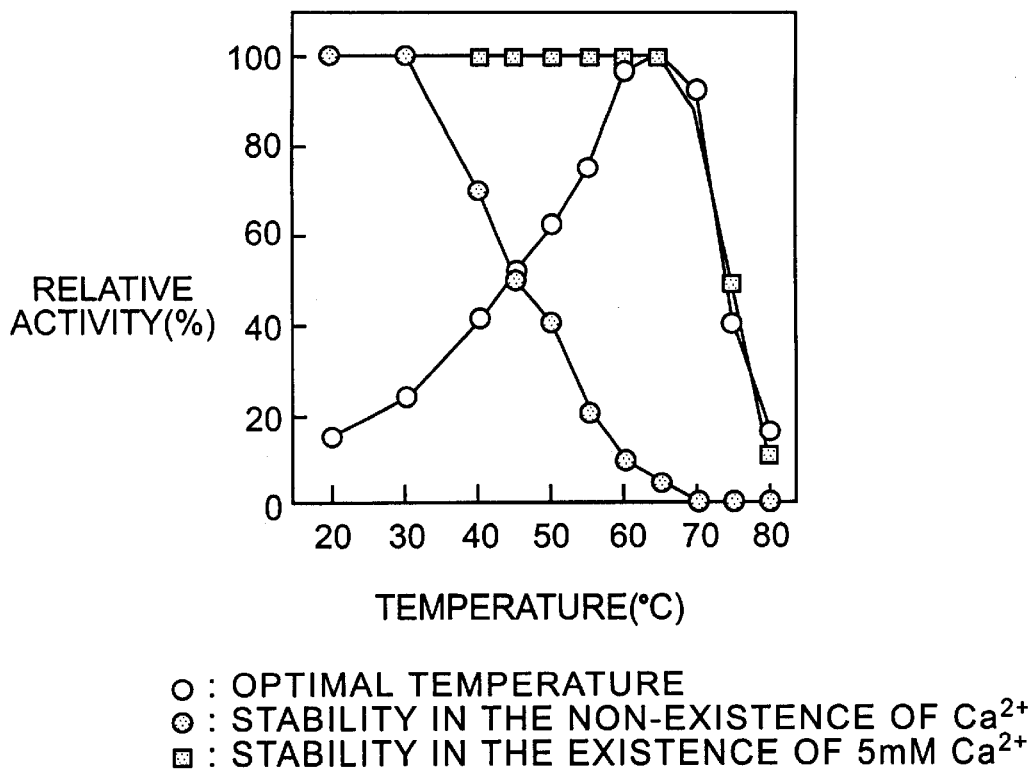
FIG. 3 is a graph measuring of novel phytase produced by Bacillus sp. DS11 (KCTC 0231BP), a novel strain, in accordance with EXPERIMENTAL EXAMPLE 2 of this invention.
Figures 2, 3:
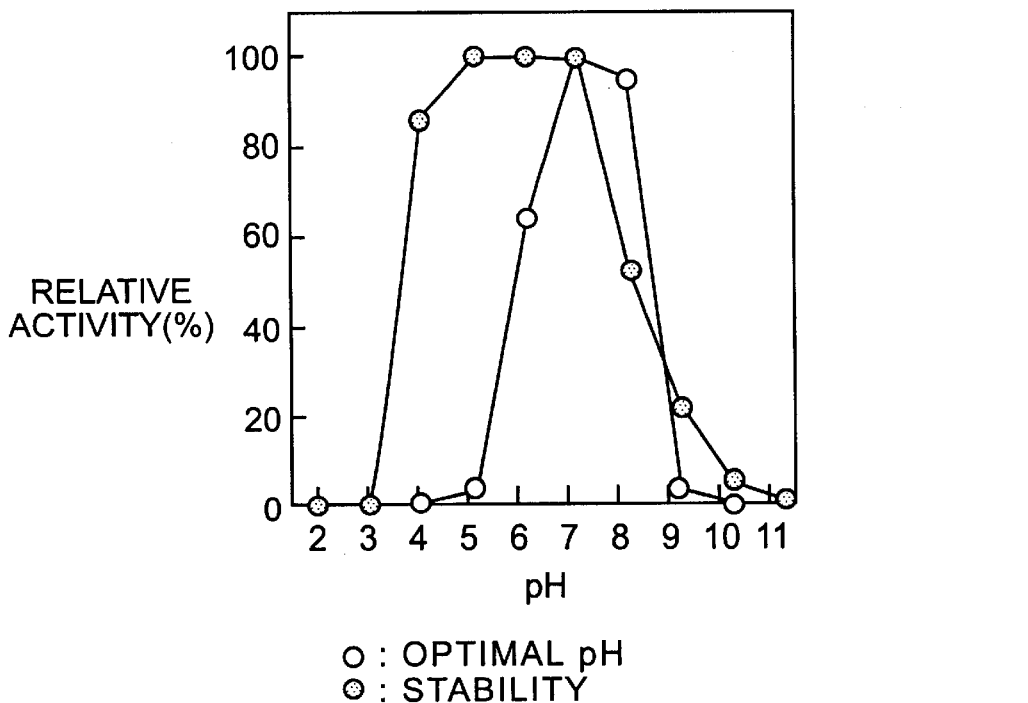

The results of phytase activity in the different conditions of pH are shown in the attached drawing FIG. 3 (3-2) and the optimal pH was 7.0. Further, to measure the stability on pH, the enzyme was left at various conditions of pH for 1 hour so as to assess the residual activity of phytase. Even under the acidic condition of below pH 4, the enzyme was proved to have higher enzymatic activity and from these results, it is judged that the novel phytase of this invention may be extremely stable under the acidic condition of stomach.

From the test results of the aforementioned temperatures and pH, it is noted that the novel phytase of this invention may be applicable as a feed additive of monogastric animals.

EXPERIMENTAL EXAMPLE 3
Influence of Metal Ion and Inhibitor on Enzyme Activity Influence of metal ion and inhibitor on enzyme activity is represented in the following table 3.

The results of table 3 show that the addition of 1 mM EDTA inhibited the entire enzyme activity and when $Cu^{2+}$, $Zn^{2+}$ and $Mg^{2+}$ were added at the concentration of 5 mM, about 50% of enzyme activity was reduced.

TABLE 3

| Additives | Concentration | |
|---|---|---|
| | 1 mM | 5 mM |
| Non-addition | 100 | 100 |
| $CuCl_2$ | 63 | 43 |
| $ZnCl_2$ | 87 | 47 |
| $MgCl_2$ | 95 | 49 |
| $MnCl_2$ | 65 | 20 |
| $LiCl_2$ | 95 | 100 |
| $HgCl_2$ | 83 | 62 |
| $CaCl_2$ | 99 | 116 |
| $RbCl_2$ | 103 | 102 |
| EDTA | 7.5 | 7.6 |
| PMSF | 86 | 88 |

EXPERIMENTAL EXAMPLE 4
Influence of Novel Phytase Added to Feed for Broiler on Environmental Contamination To estimate the influence relation of availability and released amounts of phosphate when phytase is added, broilers were divided into three groups such as novel phytase group, soybean-extracted plant phytase group and mold phytase group on the market (manufacturer: Sigma). Each of hatched-out 200 males of Avaachre broiler chicken was announced publicly for this experiment. The cultured medium containing phytase was ultrafiltrated and further concentrated at low temperature under vacuum and dried by lyophilizer. Each 500 unit of this lyophilized phytase was added to per kg of feed. The same amount of soybean phytase or mold phytase as above was also added to the feeds and the results were represented in the following table 4.

TABLE 4

| Classification | Plant (soybean) phytase | Commercial mold phytase | Novel phytase |
|---|---|---|---|
| Phosphate contents in feeds (g/kg) | 5.5 | 5.5 | 5.5 |
| Intake of total feeds (g/kg) | 2.7 | 2.7 | 2.7 |
| Intake of phosphate (g/head) | 15.1 | 15.2 | 15.1 |
| Accumulation of phosphate (g/head) | 7.1 | 7.8 | 8.8 |
| Discharge of phosphate (g/head) | 8.0 | 7.4 | 6.3 |
| Absorption of phosphate (%) | 47 | 51 | 58 |

The results of Table 4 revealed that when novel phytase was fed to monogastric animals, the phosphate contents released were lower than the soybean group or mold phytase group, since the phosphate availability in the former was higher than that of the latters; Namely, the activity of novel phytase was superior under acid-fast and acidic conditions and phytictaine within the grains was degraded in the intestine of animals by the novel phytase in more effective manner.

[Sequence table]
Sequencing No.: 1
Sequencing length: 15
Sequencing form: amino acid Shape: straight chain
Sequencing type: protein
Sequence: Ser-Asp-Pro-Tyr-His-Phe-Thr-Val-Asn-Ala-Ala-Xaa-Glu-Thr-Glu
Sequencing No.: 2
Sequencing length: 11
Sequencing form: amino acid
Shape: straight chain
Sequencing type: protein Sequence: Ser-Glu-Pro-Glu-Leu-Lys-Leu-Glu-Ala-Val-Val
Sequencing No.: 3
Sequencing length: 12
Sequencing form: amino acid
Shape: straight chain
Sequencing type: protein
Sequence: Pro-Ala-Ser-Arg-x-Gin-Ser-Ser-Cys-Asp-Thr-Val

What is claimed is:

1. A biologically pure culture of Strain Bacillus sp. DS11 (KCTC 0231BP).

2. An isolated phytase produced by the Bacillus sp. of claim 1 wherein the phytase has all of the following identifying characteristics:

Optimal temperature 65° C.

Optimal pH 7.0

Molecular Weight 43,000 daltons

Isoelectric point 5.6

Sequence of N-terminal amino acid SEQ ID NO: 1.

3. The method of using the isolated phytase, produced by strain Bacillus sp. DS11 (KCTC 0231BP), of claim 2 as a feed additive comprising:

a. preparing the phytase and b. adding it to feed.

* * * * *